United States Patent [19]

van Leeuwen

[11] Patent Number: Plant 6,382

[45] Date of Patent: Nov. 8, 1988

[54] ALSTROEMERIA NAMED FLAMENGO

[75] Inventor: Jac. van Leeuwen, Poeldijk, Netherlands

[73] Assignee: Lezan V.O.F., Hillegom, Netherlands

[21] Appl. No.: 2,552

[22] Filed: Jan. 12, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new and distinctive variety of alstroemaria of the butterfly type particularly distinguished by its continuous year-around and profuse production of very large flowers of a distinctive Amaranth rose and Spinel red on white coloration of the uppermost petals, the flowers being borne singly on strong, short peduncles comprising an umbel formation carried on strong, relatively tall canes and the flowers having very good lasting quality both on the plant and as cut flowers.

1 Drawing Sheet

BACKGROUND OF THE NEW PLANT

This new butterfly type alstroemeria hybrid originated as a seedling of unknown parentage discovered in our greenhouse at Hillegom, Holland, growing among a group of alstroemeria seedlings of various alstroemeria plants maintained for breeding purposes. This particular seedling was selected by me for propagation because of the very unusual coloring of pink on white and the very large size of the flowers. Propagation of this discovery was carried on by me by root or rhizome division and such propagation was carried on through several successive generations whereby it was conclusively determined that the novel and distinctive characteristics of the discovery plant were carried on from generation to generation and appeared to be firmly fixed. This new alstroemeria cultivar is now being grown both at Hillegom and at Aalsmer, Holland.

DESCRIPTION OF THE DRAWING

My new alstroemeria cultivar is illustrated by the accompanying photographic drawing, which shows a face view of one of the flowers illustrating the distinguishing color characteristics and flower form of the blossoms, the color rendition being as nearly true as it is reasonably possible to obtain by conventional photographic procedures.

DESCRIPTION OF THE NEW PLANT

The following is a detailed description of my new alstroemeria cultivar with the color designations being according to The R.H.S. Colour Chart of The Royal Horticultural Society of London, England.

THE PLANT

Origin: Seedling.
Parentage: Unknown.
Classification:
- *Botanic.*—Alstroemeria Hybrid (Butterfly Type).
- *Commercial.*—Butterfly Alstroemeria.

Form: Bush, like a perennial plant.
Height: About 120 cm.
Main stem or cane length: Averaging about 150 cm.
Branching character: Numerous stems from one plant.
Growth: Very strong and upright.
Foliage:

- *Quantity.*—Moderate.
- *Number of leaves.*—One pair at each internodium.
- *Leaf size.*—About 9 cm. long.
- *Leaf shape.*—Oval with entire margin.
- *Texture.*—Leathery.
- *Aspect.*—Shiny.
- *Color.*—Upper side — Dark green. Under side — Medium green.

Rhizomes:
- *Size.*—About 9 to 11.5 cm. long, depending upon season.
- *Color.*—Pale white.

THE BUD

Form: Ovid, sometimes elliptic.
Size: About 3½ cm. long.
- *Diameter.*—About 14 mm.

Opening rate: Normal.
Color: When petals begin to unfurl, the color is turning from red to salmon pink.
Sepals:
- *Number.*—Six.
- *Shape.*—Cuneate; when flowers open, the sepals curl back.

Peduncle:
- *Length.*—About 7.6 cm.
- *Character.*—Rigid.
- *Color.*—Medium green.

THE FLOWER

Blooming habit: Continuous and profusely.
Size: Very large.
Borne: In am unbel cluster.
Shape:
- *When bloom first opens.*—Cup-shaped.
- *When bloom matures.*—Somewhat flat.

Petalage:
- *Number of petals.*—Six.
- *Shape.*—Cuneate, with somewhat ruffled margins and a rather flat apex.
- *Texture.*—Leathery.
- *Aspect.*—Shiny.
- *Color.*—Outer Petals: Main color, whitish with flush of 62B-65A at the inner portion of the petal body and a big purplish-red blotch, 54A-B, at the center of the outer end portion with longitudinally extending stripes at the outer end margins. Inner Petals: Mainly white with central brush of 53B-C at base and tip and many brown stripes from end to end of petal body.

Peduncle:

*Length.*—Short, about 7.5 cm. long.

*Strength.*—Very strong and upright.

*Color.*—Medium green with anthocyane coloring.

Diseases resistance: Resistant to *Fusarium oxysporum* as observed in the Netherlands.

Lasting quality: Very good, both on the plant and as a cut flower.

REPRODUCTIVE ORGANS

Stamens:

*Number.*—Six.

*Arrangement.*—Around the pistil.

*Anthers.*—Size: About 1.3 cm. Color: Light purple.

*Filaments.*—Length: 1.3 cm. Color: Yellow green.

*Pollen.*—Color: Light purple.

Pistils:

*Number.*—One.

*Style.*—Length: About 3.8 cm. Color: Light purple.

Stigmas.—Color: Light purple.

Characteristics of ovaries: A light green color; there is an anthocyane shade, but not strong, on and between the ribs.

FRUIT

Fertility: The fruit is fertile.

Shape: Ovoid.

Color at maturity: Green.

This new alstroemeria variety is not comparable with any other and it is superior in plant form, stem, color and blooming habit.

I claim:

1. A new and distinctive alstroemeria variety, substantially as herein shown and described, characterized by its butterfly form and abundant production of very large flowers particularly distinguished by the generally whitish color of the upper petals, the outer center portion of which bear a large, reddish spot and the petal body being heavily marked by brownish stripes extending radially from the petal base toward the outer margins.

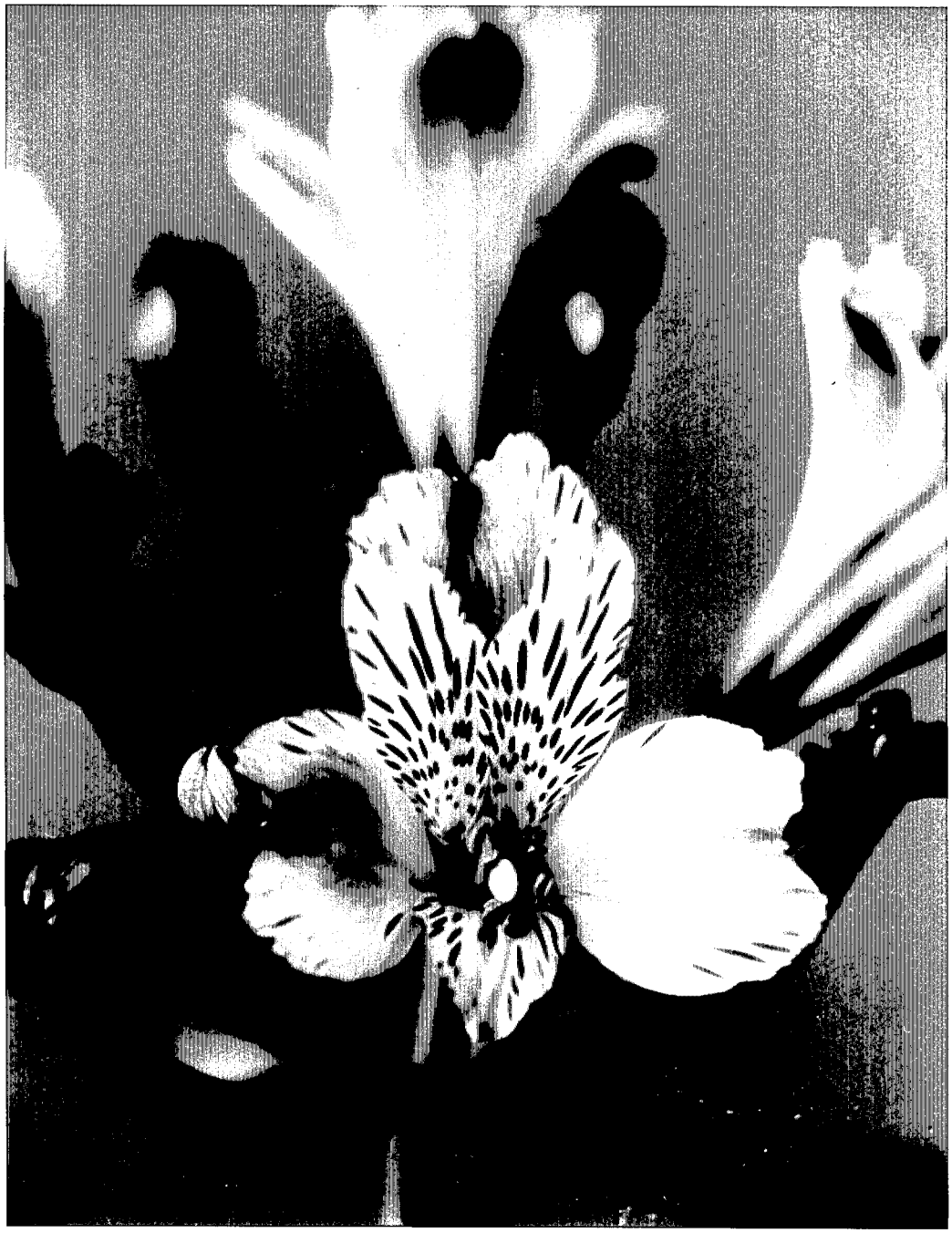

* * * * *